United States Patent
Balogh et al.

(10) Patent No.: US 6,509,419 B1
(45) Date of Patent: *Jan. 21, 2003

(54) CHEMICALLY MODIFIED POLYETHYLENE OXIDE COMPOSITIONS WITH IMPROVED ENVIRONMENTAL STABILITY

(75) Inventors: Bridget A. Balogh, Menasha, WI (US); Vasily A. Topolkaraev, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/904,381

(22) Filed: Jul. 12, 2001

(51) Int. Cl.$^7$ .......................... C08L 29/00; C08L 33/02; C08L 33/18; C08L 33/20
(52) U.S. Cl. ................ 525/221; 525/231; 525/238; 525/241; 428/332; 428/338; 428/339
(58) Field of Search ................ 525/221, 231, 525/238, 241; 428/332, 338, 339

(56) References Cited

U.S. PATENT DOCUMENTS

| | | | |
|---|---|---|---|
| 3,676,529 A | | 7/1972 | Fall |
| 3,833,708 A | | 9/1974 | Miller et al. |
| 3,891,584 A | | 6/1975 | Ray-Chaudhuri et al. |
| 3,957,605 A | | 5/1976 | Assarsson et al. |
| 3,963,805 A | | 6/1976 | Chu |
| 3,976,607 A | * | 8/1976 | Hokama et al. ............ 525/222 |
| 4,018,729 A | | 4/1977 | Faucher et al. |
| 4,206,155 A | | 6/1980 | Korber |
| 4,619,988 A | | 10/1986 | Leung et al. |
| 4,725,492 A | | 2/1988 | Yazaki et al. |
| 4,810,612 A | | 3/1989 | Ueda et al. |
| 5,209,849 A | | 5/1993 | Hu et al. |
| 5,342,861 A | | 8/1994 | Raykovitz |
| 5,360,419 A | | 11/1994 | Chen |
| 5,364,907 A | | 11/1994 | Rolando et al. |
| 5,367,003 A | * | 11/1994 | Petcavich ............ 523/124 |
| 5,385,974 A | | 1/1995 | Ohmae |
| 5,641,562 A | * | 6/1997 | Larson et al. ............ 442/394 |
| 5,700,890 A | * | 12/1997 | Chou ............ 526/266 |
| 5,998,546 A | * | 12/1999 | Li et al. ............ 525/192 |
| 6,063,866 A | | 5/2000 | Wang et al. |
| 6,110,849 A | * | 8/2000 | Tsai et al. ............ 428/357 |
| 6,117,947 A | | 9/2000 | Wang et al. |
| 6,172,177 B1 | | 1/2001 | Wang et al. |
| 6,214,933 B1 | | 4/2001 | Wang et al. |
| 6,225,406 B1 | | 5/2001 | Wang et al. |
| 6,255,386 B1 | | 7/2001 | Wang et al. |

FOREIGN PATENT DOCUMENTS

| | | |
|---|---|---|
| AU | 52355/93 | 3/1994 |
| DE | 1806165 | 5/1969 |
| EP | 0488119 | 6/1992 |
| GB | 2070046 | 9/1981 |
| JP | 8-311719 | 11/1996 |
| WO | WO 94/00163 | 1/1994 |
| WO | WO 94/00293 | 1/1994 |
| WO | WO 95/20615 | 8/1995 |
| WO | WO 96/21057 | 7/1996 |

OTHER PUBLICATIONS

Mortensen, Kell et al. Phase Behavior of Poly(propylene Oxide)–Poly(ethylene oxide)–Poly(propylene oxide) Triblock Copolymer Melt and Aqueous Solutions. *Macromolecules* vol. 27, 20 pp. 5654 Jan. 1, 1994.

Hu, Guo–Hua et al. Free Radical Grafting of Chemically Activated Maleic anhydride onto Polypropylene by Reactive Extrusion—abstract only. *Annu. Tech. Conf.—Soc. Plast. Eng.* vol. 3 pp. 2775–8 Jan. 1, 1994.

Sperling, L.H. Graft Copolymers *Introduction to Physical Polymer Science*, Chapter 2, Section 2.7.2, pp. 44–47 Jan. 1 1986.

* cited by examiner

*Primary Examiner*—Nathan M. Nutter
(74) *Attorney, Agent, or Firm*—Kilpatrick Stockton LLP

(57) ABSTRACT

Novel polymer blends useful for manufacturing breathable, environmentally stable, and water weakenable disposable films, fibers, and articles, and methods for making the blends are disclosed. The films, fibers and articles manufactured from these novel blends demonstrate improved stability and enhanced strength when exposed to environmental conditions of increased humidity and elevated temperature. Films, fibers, and articles manufactured from the novel polymer blends are particularly useful for the manufacture of disposable products.

11 Claims, 1 Drawing Sheet

CHEMICALLY MODIFIED POLYETHYLENE OXIDE COMPOSITIONS WITH IMPROVED ENVIRONMENTAL STABILITY

FIELD OF THE INVENTION

The present invention relates to novel polymer blends for manufacturing breathable and environmentally stable water weakenable disposable films, fibers and articles and the methods for making those blends. Particularly, the present invention relates to breathable, environmentally stable water weakenable polymer blends capable of imparting breathable and environmentally stable water weakenable films, fibers, and articles with improved stability and enhanced strength when exposed to environmental conditions of increased humidity and elevated temperature.

BACKGROUND OF THE INVENTION

Disposable products are a great convenience and provide the benefit of one time, sanitary use. Such products can be useful for applications including, but not limited to, personal care items, diapers and training pants, feminine care products, adult incontinence products, hospital garments, wound care products, hospital bed linens, surgical fabrics, medical fabrics, and the like. However, there is concern about the disposal of these products because of traditional disposal methods. For instance, incineration of these products is not desirable because of increasing concerns about air quality, and the costs and difficulties associated with separating these products from other disposed, non-incineratable articles. Dumping of these products is also undesirable due to limited landfill space and increasing land cost. Consequently, there is a need for disposable products which may be quickly and conveniently disposed of by means other than dumping or incineration.

It has been proposed to dispose of these products in municipal and private sewage systems. Ideally, these products could be discarded by means of water and, for example, would be water weakenable and flushable in conventional sewage systems. Articles suited for disposal in sewage systems that can be flushed down conventional toilets are termed "flushable." Disposal by flushing provides the additional benefit of providing a simple, convenient and sanitary means of disposal. However, all disposable products, and especially flushable products, must have sufficient strength to perform under the conditions in which they will be used. Thus, it is desirable for disposable products to withstand the elevated temperature and increased humidity conditions encountered during use, yet lose integrity upon contact with water such as, for example, in a toilet.

It is also desirable that these disposable products are breathable in order to increase the level of comfort of the consumers of these products. Many disposable articles are not designed for the comfort of the user. Many of these articles use thermoplastic polymers which do not have high water vapor transmission rates and therefore do not have good breathability. In the case of many disposable products, breathability is especially desirable in order to avoid the build-up of perspiration. By increasing the breathability of the films that comprise these products, the skin wellness of the user is also increased. It is desirable for the water vapor to pass through the film and move away from the skin rather than becoming trapped against the skin where it can cause possible rashes or other skin maladies. However, it would not be desirable for the film to disintegrate when exposed to the water vapor. Therefore, it is desirable for the article to be comprised of a breathable material which has mechanical integrity when it is dry, yet it is readily water weakenable upon immersion in water. Furthermore, it is highly desirable if the film demonstrates the stability and strength to withstand the environmental conditions of elevated temperature and increased humidity that are often experienced in many end-use situations, such as, for instance, in the use of personal care products.

Polyethylene oxide (PEO) is a commercially available thermoplastic water-soluble resin that is desirable for disposable applications. It is also desirable as a component material for flushable applications, due to its unique interaction with water and body fluids. PEO, which is represented by the following formula:

can be produced from the ring opening polymerization of the ethylene oxide,

Because of its water-responsive properties, PEO is desirable for flushable applications. However, commercially available PEO resins are very sensitive to high humidity and elevated temperature environments which limits its use in many disposable products.

Because of today's global market, it is necessary to manufacture, ship and store product components, and end-use products all over the world, encompassing a multitude of climatic conditions. PEO films dramatically lose strength and rigidity when the humidity is above about 65% Relative Humidity (RH) and at temperatures of between about 35–55° C. because of the resulting increased moisture absorption. As a result, PEO films experience more failure and tear more easily during manufacturing and storage under these conditions of increased humidity and elevated temperatures. Especially noticeable are stress induced environmentally accelerated cracking and tearing which increases as the material ages.

These environmentally induced failures significantly limit the flexibility needed to manufacture, distribute, and sell disposable, flushable products. The film used for flushable products is usually folded, rolled or bent and then stored in warehouses until the end-use product is scheduled to be manufactured. The most cost effective storage space is generally not environmentally controlled and is subject to elevated temperatures and increased humidity. Such an environment accelerates the cracking and tearing of PEO films which often makes the films unsuitable for manufacture.

Shipping and storage of finished products can also cause environmentally induced tearing and cracking when the end use products are exposed to increased humidity and elevated temperature during shipment throughout the world and storage in distribution warehouses in various climates. Controlling the shipping and storage environment would significantly increase the cost of distribution.

Products that were subjected to increased humidity and elevated temperatures may also experience a higher incidence of failure during use causing consumer dissatisfaction. Furthermore, these problems all increase with aging of the product, limiting the length of time products could be stored before sale. These environmentally induced failures significantly limit the application of PEO, especially as a component of flushable products, because elevated temperature and increased humidity are often experienced during the manufacture, distribution and use of such products and result in performance failure.

Many have attempted to overcome these difficulties. The current state of the art includes disposable articles consisting of a liquid impermeable, vapor permeable film consisting of a crystallizable, stretched polyolefin-based film and a rattle-reducing additive which is poly(ethylene oxide). However, these liquid impermeable, vapor permeable films require at least one nucleating agent which is described as talc or calcium carbonate. Further, stretching is required to generate porosity and hence breathability and subsequent leaching of the rattle-reducing agent is desired. These are also coated, transparent plastic articles that may consist of poly(ethylene oxide). An inorganic, protective coating is applied as a separate layer over the transparent plastic article to improve surface hardness, increase stretch resistance, and facilitate non-fogging. The inorganic, protective coating can comprise various metal oxides. However, the coating forms a separate, discrete, glass-like layer from the transparent plastic article and the resulting coating and articles are not breathable or flushable.

Multilayered or coated recording sheets are available for electrostatic printing processes. The recording sheets consist of a base sheet with an anti-static layer, which can be made from poly(ethylene oxide). The recording sheets consist of an additional toner-receiving layer, which consists of inorganic oxides such as silicon dioxide, titanium dioxide, calcium carbonate, or the like. The poly(ethylene oxide) and inorganic oxides are contained in separate layers, the anti-static layer and the toner-receiving layer respectively. Further, the recording sheets are not breathable or flushable.

Thus, currently available polymer films are not practical for applications that are water-weakenable and breathable because they do not demonstrate improved stability and enhanced strength when exposed to environmental conditions of elevated temperatures and increased humidity. What is needed in the art, therefore, is a polymer capable of making water-weakenable and breathable films, fibers and articles that have improved stability and enhanced strength when exposed to environmental conditions of elevated temperature and increased humidity. Further, what is needed in the art is a means to efficiently and economically produce a polymer capable of forming water weakenable and breathable films, fibers and articles that have improved strength when exposed to environmental conditions of increased humidity and temperature.

SUMMARY OF THE INVENTION

The invention relates to novel PEO blends capable of comprising environmentally stable water weakenable and breathable films, fibers, and articles that demonstrate improved stability and enhanced strength when exposed to environmental conditions of increased humidity and elevated temperature. The invention also relates to processes and methods for manufacturing the novel blends. The novel PEO blends can be useful for manufacturing products that require disposal, including but not limited to, personal care items, diapers and training pants, feminine care products, adult incontinence products, hospital garments, wound care products, hospital bed linens, surgical fabrics, medical fabrics, and the like. Desirably, the novel PEO blends can be composed of chemically modified PEO resin and thermoplastic synthetic resins.

The polymer blends of the present invention can be used to produce a breathable, environmentally stable water weakenable film that does not require stretching and/or addition of filler to provide breathability. The novel blends can also provide stronger films with significantly enhanced tensile yield load, to prevent cracking and tearing when subjected to environmental stress during manufacturing, shipping and storage. Concurrently, the novel blends provide films that are water weakenable, making them desirable for disposable applications such as flushable products.

The invention also relates to films, fibers, and articles manufactured from the novel polymer blend compositions. These films, fibers, and articles are breathable, stable and water weakenable and demonstrate improved stability and enhanced strength when exposed to environmental conditions of increased humidity and elevated temperature. Desirably, these films, fibers, and articles can be used for disposable applications.

DETAILED DESCRIPTION OF THE INVENTION

Figure 1:
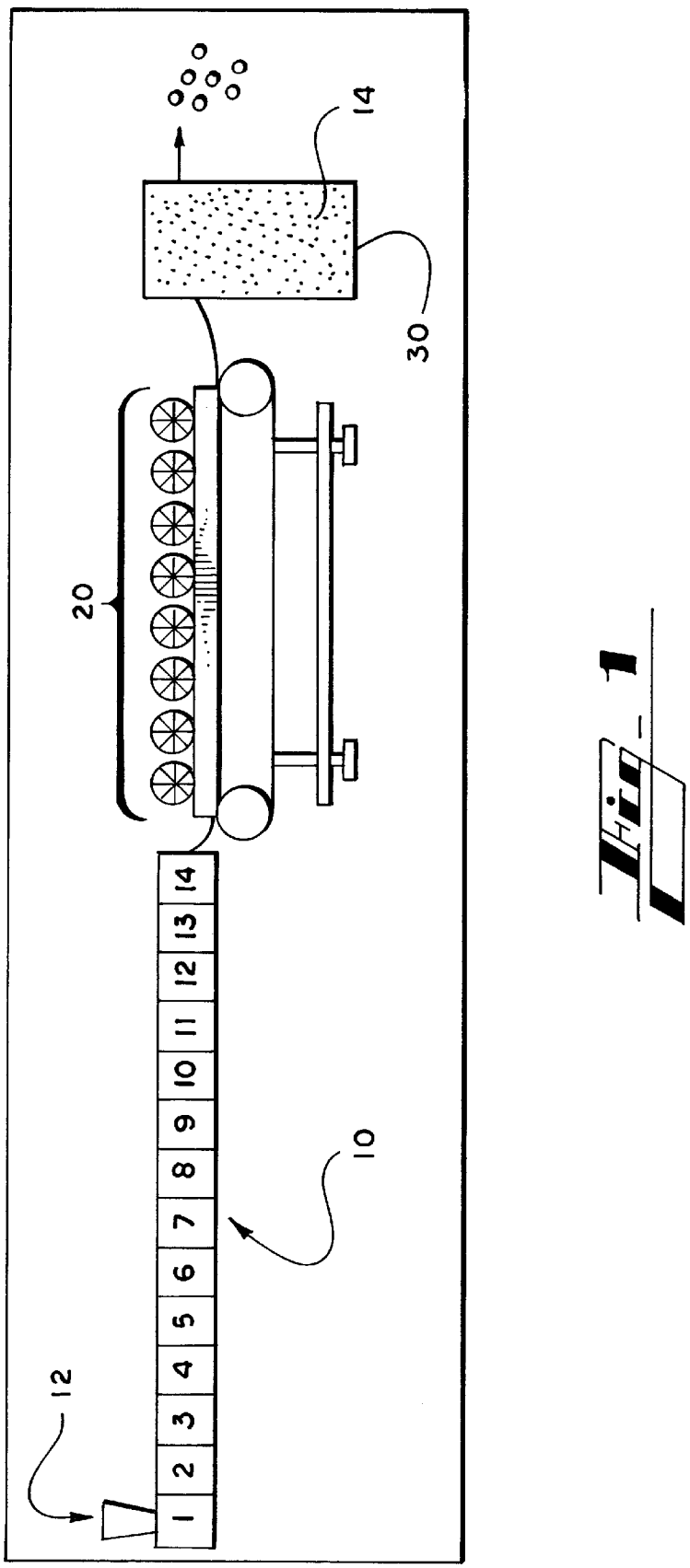
FIG. 1 shows a process diagram for forming the polymer blends including a twin screw extruder for compounding components, an air cooled belt for collecting and cooling the polymer blend, and a pelletizer.

The present invention is directed to novel polymer blends for films, fibers, and articles that are water weakenable and breathable and demonstrate improved stability and enhanced strength when exposed to environmental conditions of increased humidity and temperature. The polymer blends can be used to make films, fibers, and articles that comprise disposable products. The structure of these films, fibers and articles will weaken when placed in water and allow disposal by flushing in a standard toilet. The enhanced strength and improved stability in environments of elevated temperature and increased humidity that is demonstrated by these blends significantly delays the tearing and cracking associated with other polymers exposed to those conditions. In addition, the water vapor transmission capabilities of the blends provide for breathability of the article and consumer comfort. The polymer blend compositions produce a breathable film that does not require stretching and/or addition of filler to provide breathability.

As used herein, the term "water-responsive" refers to polymers, films, fibers, articles, and the like that are water-soluble, water-dispersible, water-disintegratable or water-weakenable. The term "water-weakenable" refers to the ability of a polymer, film, fiber and article, to remain in one piece, but weaken, lose rigidity after five minutes of immersion in water, and become drapeable. In other words, the article bends without an external force applied thereto when it is held by one corner in a horizontal position. The term "water-stable" refers to a polymer, film, fiber and article, which does not become drapeable after five minutes of immersion in water and remains in one piece after a water response test. As used herein, the term "water-dispersible" refers to the ability of a polymer, film, fiber and article, to dissolve or break into pieces smaller than 20 mesh after being immersed in water for approximately thirty minutes. The term "water-disintegratible" refers to the ability of a polymer composition, film, fiber, and article to break into multiple pieces within thirty minutes of immersion in water, wherein that some of the pieces are caught by a 20 mesh screen without slipping through. As used herein, the term "environmentally stable" refers to the ability of a film or fiber to retain shape and strength properties under load, and at elevated temperature and humidity. As used herein, the term "elevated temperature" refers to temperatures between greater than about 25° C. and about 37° C. As used herein, the term "elevated humidity" refers to the relative humidity greater than about 50% to about 80%. As used herein, the term "under load" refers to any load between 15% and up to 30% of normalized yield load (NYL).

The novel polymer blends of the present invention can comprise an water-responsive polymer. The selection of the water-responsive polymer is based on consideration of key variables such as water solubility, average molecular weights, melt processability, strength and ductility. Preferably, the water-responsive polymer comprises a polymer of ethylene oxide. As used herein, the term "polymer" includes homopolymers, copolymers, terpolymers and modifications thereof. Such water-responsive polymers include, but are not limited to, polymers of ethylene oxide, and polymers of poly vinyl alcohol. Most preferable are polymers of ethylene oxide, particularly homopolymers and modified homopolymers of ethylene oxide. Even more preferably, the water-responsive polymer is poly(ethylene oxide) ("PEO"). Preferably, the PEO is in the form of high molecular weight PEO resins. The PEO resins useful for this invention preferably have a molecular weight from greater than about 100,000 g/mol to about 8,000,000 g/mol. Although high molecular weight PEO resins are desirable for mechanical and physical properties, low molecular weight PEO resins provide the best balance between the mechanical/physical properties and the film-forming properties. As a result, the more preferred range of molecular weights of PEO resins ranges from about 300,000 g/mol. to about 1,000,000 g/mol. However, while PEO is the preferred water responsive polymer, the composite films of the present invention may also comprise other water responsive polymers.

Commercial PEO resins having a molecular weight higher than 600,000 g/mol have poor melt processability in both filler compounding and in film extrusion. This causes high melt pressure and the resulting films have severe melt fracture. Films thinner than 8 mils cannot be obtained. Therefore, the unmodified PEO resins have limited utility in making thin breathable films. Thin films are desired for personal care product applications due to better flexibility of the material and reduced finished product weight and cost. To resolve these problems, it was discovered that chemically modified PEO resins are especially useful and preferred for the breathable flushable films applicable to the present invention. These PEO resins have been modified by grafting a polar vinyl monomer onto the PEO. These modified PEO resins have lower molecular weights than the unmodified high-strength PEO resins. However the modified PEO resins have lower melt viscosities, higher melt strengths and higher melt elasticity than the unmodified low-strength PEO resins, thereby allowing the formation of very thin films of thickness of about 1 mil. When used in conjunction with the present invention, the resulting compositions can be used to produce very thin films having high degrees of breathability, flushability and ductility. The grafting modification method imparts stretchability to the PEO resin as compared to unmodified PEO resin. The process for making modified PEO resins and examples of such compositions are described in U.S. Pat. No. 6,172,177 to Wang et al., issued Jan. 9, 2001, and U.S. Pat. No. 6,117,947 issued Sep. 12, 2000 to Wang et al, both of which are herein incorporated by reference.

PEO resins suitable for this invention are available from Union Carbide Chemicals & Plastics, Inc. under the trade name Polyox®. Examples of suitable PEO resins available from Union Carbide include, but are not limited to, resins sold under the following trade designations and reported average molecular weights: POLYOX® WSR N-80, a 200,000 g/mol PEO; POLYOX® WSR N-750, a 300,000 g/mol PEO; POLYOX® WSR N-3000, a 400,000 g/mol PEO; POLYOX® WSR 205 a 600,000 g/mol PEO; POLYOX® WSR N-12K a 1,000,000 g/mol PEO; POLYOX® WSR N-60K a 2,000,000 g/mol PEO; POLYOX® WSR N-301 a 4,000,000 g/mol PEO; and POLYOX® WSR N-308 a 8,000,000 g/mol PEO. (See also POLYOX®: Water Soluble Resins, Union Carbide Chemicals & Plastic Company, Inc., 1991 which is incorporated by reference herein in its entirety.) All of the PEO resins were supplied in powder form by Union Carbide. Both PEO powder and pellets of PEO were utilized in the examples of the present invention.

PEO can be blended with any water insoluble polymer which can provide the film, fiber or article of the resulting blend with the properties of increased strength and improved environmental stability in increased humidity and elevated temperature, in addition to the properties of being water weakenable and breathable for use in film, fiber, or articles for disposable applications. Preferable are thermoplastic copolymers that are water insoluble. More preferable are ionomer resins, and polystyrene copolymers. Most preferable are ionomer resins and polystyrene acrilonitrile resins.

Most preferable, the blends can be comprised of chemically modified PEO resin and non-water-soluble ionomer or styrene acrylonitrile resin. While not proposing to be bound by any particular theory, both non-water-soluble resins are believed to provide strong intermolecular interactions with PEO thus stabilizing it in high humidity and elevated temperature environments. Desirably, the blend comprises from about 5 weight percent to about 45 weight percent of non-water soluble resin to the total weight of the blend. Blends containing more than about 45 weight percent can be too stable and lose the water weakenable characteristics. Blends comprising less than about 5 weight percent do not provide enough environmental stability when subjected to elevated temperature and high humidity. Most preferable are blends comprising from about 10 weight percent to about 30 weight percent of non-water soluble resin to total weight of the polymer blend. More preferable are blends comprising from about 10 weight percent to about 20 weight percent of non-water soluble resin to total weight of the polymer blend. The PEO blend technology can be utilized in a wide variety of thermally processable PEO-based materials where enhanced strength, stiffness and environmental stability at high humidity and elevated temperature are desirable.

Any polystyrene copolymer which increases the stability and enhances the strength of PEO blends in environments of increased humidity and elevated temperature can be used. Most preferable are styrene acrylonitrile copolymer (SAN) resins which have glass transition temperatures above the melting temperature of PEO, and below the desired extrusion processing temperature. For purposes of examples of this invention, Dow Chemical SAN copolymer resins under the trade name Tyril® were used. The styrene acrylonitrile resin used in this invention was Tyril® 125. Other SAN copolymer resins such as Dow Chemical Tyril® 880 and Tyril® 990 can be used.

Desirably, ionomer resins made from ethylene acid copolymers in which the acid groups are partially neutralized with either zinc, sodium or other ions can be used for this invention. The ionomer resins used for purposes of examples of this invention were Surlyn® 1601 (sodium ion) and Surlyn® 1652 (zinc ion) available from DuPont.

Optionally, the PEO resins employed in the polymer blends, films, fibers and articles of the present invention can contain various additives including, but not limited to, plasticizers, processing aids, fillers, dispersants, solid state modifiers, rheology modifiers, antioxidants, UV light stabilizers, pigments, colorants, slip additives, antiblock agents, polymer emulsions, and the like.

For example, the polymer blends of the present invention can include filler. The selection of a filler material is based on consideration of key parameters such as particle size, expansion and swelling efficiency, and interaction with the polymer. Suitable filler materials can be organic or inorganic, and are desirably in a form of individual, discreet particles. Suitable inorganic filler materials include metal oxides, metal hydroxides, metal carbonates, metal sulfates, various kinds of clay, silica, alumina, powdered metals, glass microspheres, or vugular void-containing particles. Particularly suitable filler materials include calcium carbonate, barium sulfate, sodium carbonate, magnesium carbonate, magnesium sulfate, barium carbonate, kaolin, carbon, calcium oxide, magnesium oxide, aluminum hydroxide, and titanium dioxide. Still other inorganic fillers can include those with particles having higher aspect ratios such as talc, mica and wollastonite. Suitable organic filler materials include, for example, latex particles, particles of thermoplastic elastomers, pulp powders, wood powders, cellulose derivatives, chitin, chitozan powder, powders of highly crystalline, high melting polymers, beads of highly crosslinked polymers, organosilicone powders, and powders of super absorbent pdymers, such as partially neutralized polyacrylic acid, and the like, as well as combinations and derivatives thereof. These filler materials can improve toughness, softness, opacity, vapor transport rate (breathability), water dispersability, biodegradability, fluid immobilization and absorption, skin wellness, and other beneficial attributes of the film.

Preferably, the filler is added in an amount sufficient to create a composite that can be made into films. Preferably, the filler comprises from about 10 percent to about 90 percent by weight of the film. More preferably, the filler comprises from about 20 percent to about 50 percent by weight of the film. PEO resins will effectively disperse the fillers during the melt extrusion process and produce extruded strands of a uniform and smooth surface.

Suitable commercially available filler materials include the following:

1. SUPERMITE®, an ultrafine ground $CaCO_3$, which is available from ECC International of Atlanta, Ga. This material has a top cut particle size of about 8 microns and a mean particle size of about 1 micron and can be coated with a surfactant, such as Dow Corning 193 surfactant, before mixing with the polymer.
2. SUPERCOAT®, a coated ultrafine ground $CaCO_3$, which is available from ECC International of Atlanta, Ga. This material has a top cut particle size of about 8 microns and a mean particle size of about 1 micron.
3. OMYACARB® UF, high purity, ultrafine, wet ground $CaCO_3$, which is available from OMYA, Inc., of Proctor, Vt. This material has a top cut particle size of about 4 microns and an average particle size of about 0.7 microns and provides good processability. This filler can also be coated with a surfactant such as Dow Corning 193 surfactant before mixing with the polymer.
4. OMYACARB® UFT $CaCO_3$, an ultrafine pigment surface coated with stearic acid, available from OMYA, Inc. This material has a top cut particle size of about 4 microns and a mean particle size of about 0.7 microns and provides good processability. In addition, the inorganic fillers may include water-soluble fillers including, but not limited to, magnesium sulfate, sodium sulfite, sodium hydrogen sulfite, sodium sulfate, sodium hydrogen sulfate, sodium phosphate, sodium hydrogen phosphate, sodium carbonate, sodium hydrogen carbonate, potassium carbonate, sodium hydroxide, potassium hydroxide, sodium chloride, potassium chloride, and, where applicable, hydrates thereof.

Optionally, it can be desirable to modify the surface of the filler with a surface modifying agent to improve the surface properties of the fillers or the resulting films. The filler can be coated with liquid additives to reduce coupling at the resin-filler interface. Decoupling should facilitate debonding of filler from polymer matrix during stretching. This is especially important for the polar PEO matrix, which demonstrates strong interaction with fillers. At the same time, the coating should provide affinity to polymer resin for improved dispersion and deagglomeration. Examples of such additives include silicone glycol copolymers of different Hydrophilic-Lipophilic Balance (hereinafter HLB) numbers ranging from 0 to about 12. Such silicone glycol copolymers are available from Dow Corning Corporation. The variation in HLB number can provide controlled interaction of the coated filler with PEO. More specifically, FF400 additive (HLB=6.6) and 193 surfactant (HLB=12) have been used to coat calcium carbonate in a solvent-surfactant solution. Filler also can be precompounded with a surfactant before mixing with PEO resin, or additive can be compounded with resin and filler at the melt-blending step. The latter method reduces effectiveness of the coating.

In addition to the novel polymer blends and the filler, the environmentally stable water weakenable and breathable films, fibers, and articles produced in the present invention may optionally contain various additives such as plasticizers, processing aids, rheology modifiers, antioxidants, UV light stabilizers, pigments, colorants, slip additives, antiblock agents, etc. which may be added before or after blending with the filler.

The process of making flushable and breathable films, fibers and articles in accordance with the present invention includes the preparation of a composite formed by blending a water responsive polymer with a water insoluble polymer. Although the present invention is demonstrated in the following examples by the use of poly(ethylene oxide), other known water-responsive polymers may be used as the base polymer component of the blend. These polymers include, but are not limited to, polymers and copolymers of ethylene oxide, particularly homopolymers, modified polymers and graft copolymers of ethylene oxide; polymers of vinyl alcohol; poly(vinyl pyrrolidone), polyethyloxazoline, and water-responsive acrylic acid based copolymers. In the examples, the water-responsive polymer is a polymer or copolymer of ethylene oxide, more particularly a homopolymer of ethylene oxide.

The selection of the water-responsive polymer is based on consideration of key variables including, but not limited to, water responsiveness, controlled molecular weight, melt processability, strength and ductility. In the following examples, several commercially available poly(ethylene oxide) resins (hereinafter abbreviated as PEO) were selected as the water-responsive polymer component of the blend. Although the present invention is demonstrated by the use of PEO as the polymer component, the scope of the present invention is not limited to PEO and can be expanded to other water responsive polymers containing polar, ionic, and cationic functional groups. Further, the PEO resin can be chemically modified by grafting, reactive extrusion, block polymerization or branching to improve its processability in a melt and performance in a solid state. The PEO resin can be modified by reactive extrusion or grafting as described in more detail in U.S. Pat. No. 6,172,177 issued to Wang et al., Jan. 9, 2001, which is incorporated by reference in its entirety herein.

The selection of water insoluble polymer is based on consideration of key variables including, but not limited to glass transition temperature, melt processability, strength and ductility. Thermoplastic synthetic resins were used in the examples. Styrene acrylonitrile copolymer (SAN) resins which have glass transition temperatures above the melting temperature of PEO, or below the desired extrusion processing temperature, are applicable for this invention. Dow Chemical manufactures SAN copolymer resins under the tradename Tyril®. The styrene acrylonitrile resin used in these Examples was Tyril® 125.

Ionomer resins made from ethylene acid copolymer in which the acid groups are partially neutralized with either zinc, sodium or other ions are applicable for this invention. Other melt processable ionomer resins may also be appropriate for this invention. The ionomer resins used in these Examples were Surlyn® 1601 (sodium ion) and Surlyn® 1652 (zinc ion) available from DuPont.

The selection of process equipment for the preparation of the water weakenable and breathable polymer blends, and films of the following examples is based on major requirements such as high shear melt processing, sufficient residence time for mixing, and potential for high rate processing. Desirably the component materials, the PEO resin, and the thermoplastic synthetic resin are suitably intermixed prior to melting. Equipment which can be used includes any suitable mixing device, such as Bradender Plasticorders, Haake extruders, single or multiple screw extruders, or any other mechanical mixing devices which can be used to mix, compound, process or fabricate polymers. Alternatively, the components of the compositions of the present invention can be fed separately into the melt processing apparatus. Conventional extruders having separate feeders which are suitable for preparing the compositions of the present invention can be used. Pelletizing the extruded polymer blend can be performed by any suitable pelletizing equipment, such as, for example, a Conair pelletizer.

The novel polymer blends were produced by a twin screw extrusion process, as demonstrated in FIG. 1 is preferred to blend or mix the components in an extruder, such as a single-screw or twin-screw extruder under appropriate temperature and shear/pressure conditions to ensure mixing. The blending process can also be performed in a batchwise mixing device, such as a melt mixer or a kneader. Modified PEO and SAN, ionomer, or EVA resins can be fed into the extruder/mixer (12) either simultaneously or in a sequence to minimize any degradation or discoloration. Optionally, additives such as antioxidants can be included to reduce thermal degradation. Next, the blend is extruded and the extruded melt strands are cooled in air using a fan-cooled conveyor belt (20). The solidified strands are then pelletized. The polymer blend pellets can then be extruded into a film.

In the present invention, the PEO, thermoplastic resins, and additives are extruded into a water-weakenable, breathable blend using a Haake TW-100 co-rotating twin-screw extruder (10). The barrel has four temperature zones, each ranging from about 150° C. to about 200° C. The blend is then pelletized in a Conair pelletizer (30). The pellets (14) are then extruded into a water-weakenable, breathable film as demonstrated by the Examples. During film extrusion, the melt pump speed was adjusted to accommodate the different flow properties of the resins. For all examples, films with a target thickness of 1 mil were collected from each resin.

Chemically modified PEO base resins were used for this invention. Batches containing 98.7 weight % WSR-205 PEO powder, 1.3 weight % $TiO_2$, 1000 ppm Irganox® 1010, 1000 ppm Irganox® 1076, and 2000 ppm Irgafos® 168 (antioxidants manufactured by Ciba Geigy) were dry blended. The dry blended powder batches were then reactively extruded with 1.5 weight % 2-hydroxyethyl methacrylate (HEMA) and 0.15 weight % peroxide and used for the Examples.

The present invention is further illustrated by the following examples, which are not to be construed in any way as imposing limitations upon the scope of the invention.

EXAMPLE 1

For Example 1, a control blend was formed from 100% by weight of the chemically modified PEO base resin. A Haake TW-100 co-rotating twin-screw extruder with screws of 300 mm in length was used to demonstrate the process of preparing the compositions. The barrel temperatures were set at 170° C., 180° C., 180° C., 190° C. The screw speed was set at 120 rpm. Modified PEO was added to the extruder using a gravimetric feeder. The extruded melt strands were cooled in air at room temperature using a fan-cooled conveyor belt. The solidified strands were then pelletized using a Conair pelletizer.

The pelletized resin was converted into film on the same Haake extruder fitted with a melt pump and 4" film die. The temperature profile used for film casting was 150° C., 160° C., 170° C., 170° C., 170° C. The screw speed was held constant at 21 rpm; the melt pump speed was adjusted to accommodate the flow properties of the resin. Films with a target thickness of 1 mil were collected.

EXAMPLE 2

For Example 2, 80% by weight of modified PEO and 20% by weight of Surlyn® 1601 were dry blended, then added simultaneously to the extruder using a gravimetric feeder. The blend was processed by a Haake TW-100 co-rotating twin-screw extruder with screws of 300 mm in length. Four zones of barrel temperatures were set at 170° C., 180° C., 180° C., 190° C. The screw speed was set at 120 rpm. The extruded melt strands were cooled in air at room temperature using a fan-cooled conveyor belt. The solidified strands were then pelletized using a Conair pelletizer.

The pelletized resin was converted into film on the same Haake extruder fitted with a melt pump and 4" film die. The temperature profile used for film casting was 150° C., 160° C., 170° C., 170° C., 170° C. The screw speed was held constant at 21 rpm; the melt pump speed was adjusted to accommodate the flow properties of the resin. Films with a target thickness of 1 mil were collected.

EXAMPLE 3

For Example 3, 70% by weight of modified PEO and 30% by weight of Surlyn® 1601 were dry blended, then added simultaneously, to the extruder using a gravimetric feeder. The blend was processed by a Haake TW-100 co-rotating twin-screw extruder with screws of 300 mm in length. Four zones of barrel temperatures were set at 170° C., 180° C., 180° C., 190° C. The screw speed was set at 120 rpm. The extruded melt strands were cooled in air at room temperature using a fan-cooled conveyor belt. The solidified strands were then pelletized using a Conair pelletizer. The pelletized resin was converted into film on the same Haake extruder fitted with a melt pump and 4" film die. The temperature profile used for film casting was 150° C., 160° C., 170° C., 170° C., 170° C. The screw speed was held constant at 21 rpm; the melt pump speed was adjusted to accommodate the flow properties of the resin. Films with a target thickness of 1 mil were collected.

EXAMPLE 4

For Example 4, 80% by weight of modified PEO and 20% by weight of Surlyn® 1652 were dry blended, then added simultaneously, to the extruder using a gravimetric feeder. The blend was processed by a Haake TW-100 co-rotating twin-screw extruder with screws of 300 mm in length. Four zones of barrel temperatures were set at 170° C., 180° C., 180° C., 190° C. The screw speed was set at 120 rpm. The extruded melt strands were cooled in air at room temperature using a fan-cooled conveyor belt. The solidified strands were then pelletized using a Conair pelletizer. The pelletized resin was converted into film on the same Haake extruder fitted with a melt pump and 4" film die. The temperature profile used for film casting was 150° C., 160° C., 170° C., 170° C., 170° C. The screw speed was held constant at 21 rpm; the melt pump speed was adjusted to accommodate the flow properties of the resin. Films with a target thickness of 1 mil were collected.

EXAMPLE 5

For Example 5, 70% by weight of modified PEO and 30% by weight of Surlyn® 1652 were dry blended, then added simultaneously, to the extruder using a gravimetric feeder. The blend was processed by a Haake TW-100 co-rotating twin-screw extruder with screws of 300 mm in length. Four zones of barrel temperatures were set at 170° C., 180° C., 180° C., 190° C. The screw speed was set at 120 rpm. The extruded melt strands were cooled in air at room temperature using a fan-cooled conveyor belt. The solidified strands were then pelletized using a Conair pelletizer. The pelletized resin was converted into film on the same Haake extruder fitted with a melt pump and 4" film die. The temperature profile used for film casting was 1 50° C., 160° C., 170° C., 170° C., 170° C. The screw speed was held constant at 21 rpm; the melt pump speed was adjusted to accommodate the flow properties of the resin. Films with a target thickness of 1 mil were collected.

EXAMPLE 6

For Example 6, 80% by weight of modified PEO and 20% by weight of Tyril® 125 were dry blended, then added simultaneously, to the extruder using a gravimetric feeder. The blend was processed by a Haake TW-100 co-rotating twin-screw extruder with screws of 300 mm in length. Four zones of barrel temperatures were set at 170° C., 180° C., 180° C., 190° C. The screw speed was set at 120 rpm. The extruded melt strands were cooled in air at room temperature using a fan-cooled conveyor belt. The solidified strands were then pelletized using a Conair pelletizer. The pelletized resin was converted into film on the same Haake extruder fitted with a melt pump and 4" film die. The temperature profile used for film casting was 150° C., 160° C., 170° C., 170° C., 170° C. The screw speed was held constant at 21 rpm; the melt pump speed was adjusted to accommodate the flow properties of the resin. Films with a target thickness of 1 mil were collected.

EXAMPLE 7

For Example 7, 70% by weight of modified PEO and 30% by weight of Tyril® 125 were dry blended, then added simultaneously, to the extruder using a gravimetric feeder. The blend was processed by a Haake TW-100 co-rotating twin-screw extruder with screws of 300 mm in length. Four zones of barrel temperatures were set at 170° C., 180° C., 180° C., 190° C. The screw speed was set at 120 rpm. The extruded melt strands were cooled in air at room temperature using a fan-cooled conveyor belt. The solidified strands were then pelletized using a Conair pelletizer. The pelletized resin was converted into film on the same Haake extruder fitted with a melt pump and 4" film die. The temperature profile used for film casting was 150° C., 160° C., 170° C., 170° C., 170° C. The screw speed was held constant at 21 rpm; the melt pump speed was adjusted to accommodate the flow properties of the resin. Films with a target thickness of 1 mil were collected.

EXAMPLE 8

Many materials can be blended with PEO at levels similar to SAN or ionomer resins without improving the environmental stability of the PEO. For Example 8, 30% by weight of the ethylene vinyl acetate (EVA) copolymer resin Levapren® 600, available from Bayer was blended with 70% by weight of modified PEO as a comparative example. The modified PEO and Levapreng® 600 were dry blended, then added simultaneously, to the extruder using a gravimetric feeder. The blend was processed by a Haake TW-100 co-rotating twin-screw extruder with screws of 300 mm in length. Four zones of barrel temperatures were set at 170° C., 180° C., 180° C., 190° C. The screw speed was set at 120 rpm. The extruded melt strands were cooled in air at room temperature using a fan-cooled conveyor belt. The solidified strands were then pelletized using a Conair pelletizer. The pelletized resin was converted into film on the same Haake extruder fitted with a melt pump and 4" film die. The temperature profile used for film casting was 150° C., 160° C., 170° C., 170° C., 170° C. The screw speed was held constant at 21 rpm; the melt pump speed was adjusted to accommodate the flow properties of the resin. Films with a target thickness of 1 mil were collected.

The blend compositions that were compounded on the Haake extruder

TABLE 1

| | Weight % | | | | |
|---|---|---|---|---|---|
| | | Monomer Resins | | SAN Resin | EVA Resin |
| Example # | Modified PEO | Surlyn® 1601 | Surlyn® 1652 | Tyril® 125 | Levapren® 600 |
| 1 (control) | 100 | 0 | 0 | 0 | 0 |
| 2 | 80 | 20 | 0 | 0 | 0 |
| 3 | 70 | 30 | 0 | 0 | 0 |
| 4 | 80 | 0 | 20 | 0 | 0 |
| 5 | 70 | 0 | 30 | 0 | 0 |
| 6 | 80 | 0 | 0 | 20 | 0 |
| 7 | 70 | 0 | 0 | 30 | 0 |
| 8 (comparative example) | 70 | 0 | 0 | 0 | 30 |

The films resulting from Examples 1 through 8 were tested for tensile properties, environmental stress cracking, water vapor transmission, and water responsiveness.

Tensile Properties

The tensile properties of the films produced in Examples 1 through 8 were assessed on a Sintech 1/D tensile tester according to ASTM Test Method D 638-91. Table 2 shows the machine direction tensile properties of the films. Blends with ionomer resins of Examples 2 through 5, and SAN resins of Examples 6 and 7, can provide stronger films with significantly enhanced tensile yield load. The PEO/SAN blends of Examples 6 and 7 demonstrate significantly stiffer films with a tensile modulus enhancement by a factor of 3 or more.

TABLE 2

| Example # | Thickness (mil) | Break Stress (MPa) | % Strain at Break | Modulus (MPa) | Energy to Break (J/cm$^3$) | Yield Load (g) |
|---|---|---|---|---|---|---|
| 1 | 1.15 | 20.1 | 878.6 | 168.6 | 121.5 | 115.2 |
| 2 | 1.68 | 17.0 | 147.9 | 214.2 | 24.7 | 206.0 |
| 3 | 1.25 | 32.4 | 70.3 | 286.3 | 18.4 | 208.7 |
| 4 | 1.38 | 21.2 | 238.4 | 205.2 | 44.5 | 171.1 |
| 5 | 1.25 | 26.6 | 182.7 | 252.3 | 42.9 | 203.7 |
| 6 | 1.35 | 28.0 | 101.3 | 620.6 | 25.8 | 278.7 |
| 7 | 1.28 | 37.2 | 58.0 | 909.0 | 19.8 | 377.5 |
| 8 | 1.20 | 16.6 | 1266.0 | 131.5 | 146.4 | 85.4 |

Environmental Stress Cracking Tests

The films produced by the methods according to Examples 1–8 were assessed for environmental stress cracking according to a modified version of ASTM Method D 5397. For this test, dogbone shaped test specimens with a length of 64 mm, a width of 3.18 mm, and an 18 mm gauge length were cut from each respective film. A 1 mm notch was then made across the narrow portion of the test area on the dogbone. The purpose of the notch was to create a localized failure area and accelerate the environmental stress failure of the films. The prepared samples were then clipped to a test apparatus and allowed to hang freely; not touching the apparatus except at the clip. Another clip, which weighed approximately 15 g, was hung from the bottom of the dogbone sample. A brass gram test weight with a hook was added to the clip, and the samples were placed in an environmental chamber set at 80% RH and 37° C. The elapsed time before sample failure was recorded. If the sample did not fail, an increased load force was added.

The films were tested at weights that were significantly lower than their dry, room temperature tensile yield load value. To determine the percentage of yield load that was being applied to the films, it was necessary to do a normalization calculation. For each sample, a normalized yield load (NYL) was calculated by adjusting for the notched width of the test specimen and any difference in thickness compared to the sample used for tensile properties analysis. The test load was then divided by the NYL value to determine the percentage of the NYL tested. This number is important because it shows that the same gram weight can create a much higher % yield load in some films compared to others. Table 3 lists the results of the environmental stress cracking test, including the load tested, the average normalized yield load of the specimens tested, and the time elapsed before the sample failed.

Films formed from water weakenable polymer blends that are not environmentally stable will demonstrate stress cracks when subjected to environments of increased humidity and elevated temperature.

modified PEO control film when exposed to environments of high humidity and elevated temperature.

While not proposing to be bound by any particular theory, it has been suggested that strong intermolecular interactions in the PEO/ionomer and PEO/SAN blends which can immobilize PEO chains are responsible for improved environmental stability, the higher tensile-yield loads, and the tensile modulus demonstrated in the blends. As an example, strong intermolecular interactions in the blend of PEO with Surlyn® 1652 ionomer resin have been demonstrated using FT-IR spectroscopy. Significant shifts in asymmetric stretching vibration of carboxylate ions ($COO^-$) was measured as a result of a strong ion-dipole interaction between the $Zn^{2+}$ charged atom of the ionomer resin and the $C_2H_4O$ polar group of the PEO molecule. The zinc content in the ionomer resin which allowed strong interactions was found to be only about 0.63%. Increases of zinc content in ionomer resin can provide additional increases in the intensity of the intermolecular interactions and allow the formation of blends with even higher environmental stability.

Water Vapor Transmission Properties

To determine the breathability of compositions in accordance with this invention, the water vapor transmission rates

TABLE 3

| Example | 10 g (25 g w/clip) | | 20 g (35 g w/clip) | | 30 g (45 g w/clip) | | 40 g (55 g w/clip) | | 50 g (65 g w/clip) | |
|---|---|---|---|---|---|---|---|---|---|---|
| | Average Normalized % Yield Load | Time (min) | Average Normalized % Yield Load | Time (min) | Average Normalized % Yield Load | Time (min) | Average Normalized % Yield Load | Time (min) | Average Normalized % Yield Load | Time (min) |
| 1 | 30.3% | 1.87 | 42.3% | 0.70 | Not tested | | Not tested | | Not tested | |
| 2 | 19.3% | 4.37 | 29.0% | 1.90 | 36.6% | 0.87 | Not tested | | Not tested | |
| 3 | 15.3% | DNF | 19.7% | DNF | 27.1% | DNF | 30.6% | 3.00 | 37.3% | 3.20 |
| 4 | 23.6% | 2.93 | 33.9% | 1.67 | 43.8% | 0.87 | Not tested | | Not tested | |
| 5 | 17.0% | DNF | 24.5% | DNF | 29.2% | DNF | 35.7% | DNF | 42.2% | 4.03 |
| 6 | 14.6% | 4.57 | 20.7% | 2.43 | 24.8% | 2.33 | Not tested | | Not tested | |
| 7 | 9.0% | DNF | 13.9% | DNF | 15.8% | DNF | 18.9% | DNF | 21.8% | 5.13 |
| 8 | 42.7% | 0.43 | 63.2% | 0.53 | 81.3% | 0.57 | Not tested | | Not tested | |

DNF = Did not Fail in 24 hr @ 80% RH, 37° C.

The modified PEO control film of Example 1 was very unstable in the environment of high humidity (80% RH) and elevated temperature (37°). With a test load of only 25 grams, or 30.3% of NYL, the modified PEO film failed in less than two minutes. Under the same load level, Examples 2, 4, and 5 lasted at least one minute longer. Examples 3, 5, and 7 did not fail at all under the 25 gram load. The comparative Example 8, failed in less than one minute. The performance of Examples 3, 5, and 7 demonstrates that adding 30% of SAN or Ionomer resin to modified PEO greatly improves stability of films at increased temperature and high humidity at low load levels. Furthermore, the SAN and Ionomer films of Examples 2–7 had much higher tensile yield load values at low humidity and at room temperature conditions than Examples 1 and 8.

Because of this, they were under much less stress than Examples 1 and 8 though the same gram load force was applied. In order to see if the SAN/Ionomer films could withstand a higher percentage of yield load than Examples 1 and 8, further experiments were conducted. Example 5, the 70/30 modified PEO/Surlyn 1652 film, performed the best. It was able to withstand a 55 gram load, 35.7% of NYL, without failure. This shows that the developed blended films can support a greater load level without failure and they can also withstand a higher percentage of yield load than the (WVTR) of the films were tested according to ASTM Test Method E 96-80. Circular samples measuring three inches in diameter were cut from each of the test materials and from a control of CELGARD® 2500 microporous film which was available from Hoechst Celanese Corporation. Individual samples of the test materials and a control material were placed across the open tops of the individual vapometer cups that contained one hundred milliliters of distilled water. The screw-on flanges were tightened to form a seal along the edges of the cup. The cups were placed in a convection type oven set at 100° F. The relative humidity within the oven was not specifically controlled. The cups were first weighed and then immediately placed into the oven. After 24 hours, the cups were removed from the oven and weighed again. The WVTR of each material was calculated based on the weight loss and WVTR of the control film, assuming the WVTR of the CELGARD® 2500 microporous film to be 5000 $g/m^2/24$ hr under predetermined set conditions. In order to normalize the WVTR readings to allow for variation in the thickness of films, the WVTR is multiplied by the thickness of film in mils. A mil is defined as 0.001 inch. The Normalized WVTR is reported in $g/m^2/24$ hr/mil. The WVTR values for the films are listed in Table 4.

TABLE 4

| Example # | Thickness (mil) | WVTR (g/m²/24 hr) | Normalized WVTR (g/m²/24 hr/mil) |
|---|---|---|---|
| 1 | 1.28 | 2632.0 | 3369.0 |
| 2 | 1.75 | 1715.1 | 3001.4 |
| 3 | 1.55 | 1195.8 | 1853.5 |
| 4 | 1.30 | 1610.1 | 2093.1 |
| 5 | 1.79 | 877.3 | 1570.4 |
| 6 | 1.33 | 1898.3 | 2524.7 |
| 7 | 1.53 | 1490.8 | 2280.9 |
| 8 | 1.15 | 2504.3 | 2879.9 |

A WVTR value of 1000 or more means that the film is considered "breathable." With the exception of Example 5, all of the films were breathable. Results indicate that Example 5 may have been affected by the thickness of the samples tested, and it is believed that a thinner film made from the same material may be breathable. Hence, the films with improved environmental stability also retained an acceptable level of breathability.

Water Response Test

The water responsiveness of the films was assessed by a modified snag test. The term "snag test" refers to a test method developed by the National Sanitation Foundation. In the snag test, a film sample was placed on a straight metal rod and placed in a bath of water. The water was stirred at a specified speed. The amount of time for the film sample to disperse was recorded. The following modifications were made to the snag test to test the films in this invention: 1.) A hook shape rod was used. 2.) The film sample was stapled to itself, to insure that it would not float loosely during testing. 3.) Distilled water was used. 4.) The water was stirred at approximately 500 rpm (measured by the dry velocity of the stir bar at the same setting). The results of the modified snag test are found in Table 5.

The following terms were used to describe the behavior of the films in water: The term "water-dispersible" means that the composition dissolves or breaks into pieces smaller than a 20 mesh screen. The term "water-disintegradible" means that the composition breaks into multiple pieces within five minutes and that some of the pieces will be caught by a 20 mesh screen. The term "water-weakenable" means that the composition remains in one piece but weakens and loses rigidity after five minutes and becomes drapeable, i.e., it bends without an external force applied to the film when it is held by one corner at a horizontal position. The term "water-stable" means that the composition does not become drapeable after five minutes and remains in one piece after the water response test.

TABLE 5

| Example # | Water Response | Comments/Observations |
|---|---|---|
| 1 | Water-dispersible | Completely disperses within minutes. |
| 2 | Water-weakenable | Immediately drapeable; after soaking, edges of film get stringy. After removal from water, film is very weak and easily deformable. |
| 3 | Water-weakenable | Immediately drapeable; holds shape. |
| 4 | Water-weakenable | Immediately becomes drapeable. After soaking, holds shape but easily comes apart with force. (Stringy structure when pulled on.) |
| 5 | Water-weakenable | Immediately becomes drapeable; film has a shiny appearance in water. Holds shape better than 80% composition, still comes apart with force, though. |
| 6 | Water-weakenable | Immediately drapeable; water became cloudy during soak. Resulting film is very stringy, but still has shape. |
| 7 | Water-weakenable | Immediately becomes drapeable; film has a shiny appearance in water. Holds shape. Can be pulled apart with light force. |
| 8 | Water-distinegradable | Immediately becomes drapeable. After Soaking, structure looks like a very weak spider web. |

Although the films with improved environmental stability are not water-dispersible, they are water-weakenable.

Various other embodiments, modifications, and equivalents of the present invention may suggest themselves to those skilled in the art without departing from the spirit of the present invention or the scope of the appended claims.

We claim:

1. A polymer blend comprising a water-responsive polymer and a thermoplastic synthetic resin;
   wherein the water-responsive polymer is modified poly (ethylene oxide);
   wherein the polymer blend is capable of being formed into films that are breathable, environmentally stable and water weakenable;
   wherein the thermoplastic synthetic resin is selected from ionomer resins made from ethylene acid copolymers that are partially neutralized with ions selected from the group consisting of zinc, sodium and calcium; and polystyrene copolymers having a glass transition temperature above a melting temperature of polyethylene oxide; and
   wherein the thermoplastic synthetic resin comprises from about 5 weight % to about 45 weight % of the weight of the total blend.

2. The film of claim 1, wherein the water responsive polymer has a weight average molecular weight of between about 100,000 g/mole and about 8,000,000 g/mole.

3. The film of claim 1, wherein the water responsive polymer has a weight average molecular weight of between about 300,000 g/mole and about 1,000,000 g/mole.

4. The polymer blend of claim 1, wherein the thermoplastic synthetic resin comprises from about 10 weight % to about 30 weight % of the weight of the total blend.

5. The polymer blend of claim 1, wherein the thermoplastic synthetic resin comprises from about 10 weight % to about 20 weight % of the weight of the total blend.

6. A polymer blend of a water-responsive polymer and a water insoluble polymer,
   wherein the polymer blend is capable of being formed into films that are breathable, environmentally stable and water weakenable;
   wherein the water-responsive polymer is modified poly (ethylene oxide); and
   wherein the water insoluble polymer is selected from ionomer resins made from ethylene acid copolymers that are partially neutralized with ions selected from the group consisting of zinc, sodium and calcium; and polystyrene copolymers having a glass transition temperature above a melting temperature of polyethylene oxide.

7. The polymer blend of claim 6, wherein the water-responsive polymer has a molecular weight of between about 100,000 g/mnole and about 8,000,000 g/mole.

8. The polymer blend of claim 6, wherein the water responsive polymer has a weight average molecular weight of between about 100,000 g/mole and about 8,000,000 g/mole.

9. The polymer blend of claim 6, wherein the water responsive polymer has a weight average molecular weight of between about 300,000 g/mole and about 1,000,000 g/mole.

10. The polymer blend of claim 6, wherein the water insoluble polymer comprises from about 10 weight % to about 30 weight % of the weight of the total blend.

11. The polymer blend of claim 6, wherein the water insoluble polymer comprises from about 10 weight % to about 20 weight % of the weight of the total blend.

* * * * *